United States Patent [19]

Koning et al.

[11] Patent Number: 4,827,933
[45] Date of Patent: May 9, 1989

[54] APPARATUS AND METHOD FOR ADJUSTING HEART/PACER RATE RELATIVE TO CARDIAC PO₂ OBTAIN A REQUIRED CARDIAC OUTPUT

[75] Inventors: Gerrit Koning, Vries, Netherlands; Edward A. Schroeppel, Miamar, Fla.

[73] Assignee: Telectronics N.V., Netherlands Antilles

[21] Appl. No.: 53,510

[22] Filed: May 15, 1987

Related U.S. Application Data

[63] Continuation of Ser. No. 926,991, Oct. 30, 1986, abandoned, which is a continuation of Ser. No. 722,310, Apr. 11, 1985, abandoned.

[51] Int. Cl.⁴ ............................................. A61N 1/36
[52] U.S. Cl. ............................................. 128/419 PG
[58] Field of Search .............................. 128/419 PG

[56] References Cited

U.S. PATENT DOCUMENTS

| | | | |
|---|---|---|---|
| 3,528,403 | 9/1970 | Imredy | 128/635 |
| 3,554,199 | 1/1971 | Auphan | 128/419 PS |
| 3,559,099 | 1/1971 | Jones | 128/419 PG |
| 3,572,315 | 3/1971 | Cullin II | 128/635 |
| 3,658,053 | 4/1972 | Fergusson | 128/635 |
| 3,710,778 | 1/1973 | Cornelius | 128/635 |
| 4,009,721 | 3/1977 | Alcidi | 128/419 PG |
| 4,148,305 | 4/1979 | Reichenwberger | 128/635 |
| 4,197,853 | 4/1980 | Parker | 128/635 |
| 4,198,851 | 4/1980 | Janata | 128/635 |
| 4,201,219 | 5/1980 | Bozal-Gonzales | 128/419 PG |
| 4,202,339 | 5/1980 | Wirtzfeld et al. | 128/419 PG |
| 4,252,124 | 2/1981 | Maurer et al. | 128/635 |
| 4,363,325 | 12/1982 | Roline et al. | 128/419 PG |
| 4,399,820 | 8/1983 | Wirtzfeld et al. | 128/419 PG |
| 4,442,841 | 4/1984 | Uehara et al. | 128/635 |
| 4,450,842 | 5/1984 | Zick et al. | 128/635 |
| 4,452,672 | 6/1984 | Parker et al. | 128/635 |
| 4,467,807 | 8/1984 | Bornzin | 128/419 PG |
| 4,488,556 | 12/1984 | Ho | 128/635 |
| 4,534,355 | 8/1985 | Potter | 128/635 |
| 4,535,774 | 8/1985 | Olson | 128/419 PG |

FOREIGN PATENT DOCUMENTS

2426904 12/1979 France .............................. 128/635

OTHER PUBLICATIONS

Parker et al "Medical and Biological Engineering and Computing" V. 16, No. 4, Sep. 1978, pp. 599–600, copy in file.

Guyton, "Textbook of Medical Physiology", 5th Ed., W. B. Saunders Co., Philadelphia, 1976, pp. 543–556, copy in file.

Jansen et al "Medical and Biological Engineering and Computing" V. 16, No. 3, May, 1978, pp. 274–277, copy in file.

Wirtzfeld et al "Pace" vol. 7, Nov.–Dec. 1984, pp. 1257–1262 copy in file.

*Primary Examiner*—William E. Kamm
*Attorney, Agent, or Firm*—Henry W. Collins; Thomas R. Vigil

[57] ABSTRACT

The apparatus for pacing a heart in accordance with the heart rate needed to produce a required cardiac output while the person is exercising, comprises a pacer adapted to be implanted in a human body and having a pulse generator and control circuitry (e.g. a microprocessor) therein, a pacing lead adapted to be implanted in a heart and having a distal electrode adapted to engage and supply pacing pulses to a right ventricle of a heart, and a pO₂ sensor for sensing pO₂ of the blood in the heart. An algorithm or routine utilizing same are stored in the control circuitry (microprocessor) and are adapted to relate pO₂ and/or ΔpO₂ with the required heart rate or change in heart rate, ΔR, needed to supply a desired cardiac output and to cause the pacer to pace the heart at the required heart rate when the heart is not naturally paced.

25 Claims, 6 Drawing Sheets

APPARATUS AND METHOD FOR ADJUSTING HEART/PACER RATE RELATIVE TO CARDIAC PO₂ OBTAIN A REQUIRED CARDIAC OUTPUT

CROSS REFERENCE TO RELATED APPLICATIONS

This is a continuation of application Ser. No. 926,991, filed on Oct. 30, 1986, now abandoned, which is a continuation of U.S. application Ser. No. 722,310 filed Apr. 11, 1985, now abandoned.

BACKGROUND OF THE INVENTION

1. Field of the Invention

The present invention relates to a pacer system which is adapted to alter the rate of pacer pulses delivered (rate of pacing pulses delivered by an artificial pacemaker) to a heart while an individual is exercising relative to, and utilizing, the partial pressure of oxygen, $pO_2$, in the blood in a heart to obtain a required cardiac output.

2. Descriptiion of the Prior Art

Heretofore patients with heart dysfunctions or heart disease such as sinus node disease have been able to live a relatively normal life with the implantation of an artificial pacemaker often referred to as a pacer. However, such pacers have not always been able to mimic the response of a normal healthy heart. A normal heart responds to exercise and stress by increasing cardiac output through increased heart rate and/or stroke volume.

In this respect, patients with sinus node disease have lost the ability to increase heart rate with exercise. Accordingly, it has become a goal of optimal pacing to provide exercise responsiveness in a pacer by sensing the need for increased cardiac output.

With a view towards obtaining this goal, a number of pacemakers have been proposed for indirectly sensing the need for increased heart rate by sensing P-waves, nerve impulses, Q-T interval, pH, oxygen saturation, respiratory rate, stroke volume, motion, atrial pressure and temperature.

A P-wave triggered artificial pacemaker adapted to be exercise responsive by responding to average atrial rate is proposed in the Knudson & Amundson U.S. Pat. No. 4,313,442.

An artificial pacemaker responsive to changes in the Q-T interval is proposed in the Rickards U.S. Pat. No. 4,228,803.

The Funke U.S. Pat. No. 4,312,355 discloses a dual pace-dual sense cardiac pacer which is able to stimulate the atrium and/or the ventricle and which is able to entrain the ventricle, when the atrial rate increases, while preventing bradycardic episodes. The pacer action is triggered by detection of naturally occurring atrial and ventricular action or pulses within a predetermined time period.

The Roline U.S. Pat. No. 4,363,325 discloses a multiple mode pacer activated to switchmodes relative to heart rate while preventing atrial bradycardia. This is achieved by mode switching of the pacer from an atrial synchronous mode to a vetricular inhibited mode. Such switch of modes is actuated when no atrial activity is sensed within a preset escape interval referred to as a hysteresis period. Reversal of the mode back to the atrial synchronous mode from the ventricular inhibited mode is actuated in response to a detected atrial rate which is higher than a preset, lower, ventricualr rate. With this mode switching, the ventricle will not be stimulated twice in quick succession, which overstimulation could cause atrial bradycardia.

The Heilman et al. U.S. Pat. No. 4,303,075 discloses a method and apparatus for maximizing stroke volume through AV pacing using an implanted cardioverter/pacer which is programmed with an AV delay tailored to the particular patient. The mechanism detects and processes the impedance of the heart across two electrodes in contact with heart muscle during each heart cycle and uses the changes from cycle to cycle to trigger the issuance of pulses from the pacer depending on the direction of the impedance changes to maximize stroke volume of the heart, which is proportional to the change in value of impedance between the minimum and maximum detected impedance per heart cycle.

A proposal for placing electrodes on the Hering's nerve which extends from receptors in the sinus and glomus carotids is disclosed in the Gonzalez U.S. Pat. No. 4,201,219.

Sensors for sensing blood pH are proposed in the Alcidi U.S. Pat. No. 4,009,721 and the Mauer et al U.S. Pat. No. 4,252,124. Alcidi controls a pacer relative to the level of blood pH sensed.

See also the article "A new pacemaker autoregulating the rate of pacing in relation to metabolic needs" by Cammilli, Alcidi and Papeschi which appeared in "Cardiac Pacing", pages 414–419 Amsterdam-Oxford: Excerpta Medica, 1977 which teaches sensing pH in the right atrium.

Another artificial cardiac pacemaker which increases pacing rate in accordance with an increase in respiration rate is proposed in the Krasner U.S. Pat. No. 3,593,718.

Pacers for sensing motion or mechanical activity are proposed in the Dahl U.S. Pat. No. 4,140,132 and the Anderson et al U.S. Pat. No. 4,428,378.

The Denniston III U.S. Pat. No. 3,815,611 discloses an apparatus which detects muscle contractions through impedance measurement. The device includes an elastomer body whose impedance changes when flexed. The elastomer body is positioned adjacent a muscle such as a heart muscle such that when the muscle contracts, the elastomer body is flexed to provide a change in impedance to a bias voltage supplied thereto. Such electrical signals can be used to control a pulse generator to generate a pulse when a specified period of time has elapsed since the latest heart activity was sensed by the elastomer body.

Heretofore it has been proposed in the Cohen U.S. Pat. No. 3,358,690 to sense pressure in the right atrium and to utilize the pressure sensed to control pacing of an electrode in the right ventricle.

Also, the Zacouto U.S. Pat. No. 3,857,399 discloses, in FIG. 19 thereof, a pressure sensor that measures either left ventricular pressure or intramyocardial pressure. One sensor is located in the myocardium or septum and the other sensor is located in the left ventricle. Apparently, the pacer coupled to these sensors responds to average base pressure over relatively long periods of time and the pacer system disclosed therein appears to be static and slowly responsive to exercise.

The Sjostrand et al. U.S. Pat. No. 3,650,277 discloses a system for reducing and controlling the blood pressure of a hypertensive patient by electrical stimulation of the carotid sinus nerves, one of the baroreceptor centers of the body. The system incorporates a pressure transducer which is connected to or applied to an artery of a patient and provides electrical signals substantially representing the instantaneous arterial blood pressure of a patient. Upon calculation of a mean arterial pressure, the system is utilized to provide a series of electrical pulses having a predetermined frequency, magnitude and amplitude through an afferent nerve, such as the carotid sinus nerve, to the heart to mimic pulses to the heart occurring naturally in patients having normal blood pressure. These pulses are provided during the first portion of each heart cycle to take over the function of controlling blood pressure that is usually provided by normally functioning baroreceptors in patients who are not hypertensive.

Another artificial cardiac pacemaker which is responsive to exercise by sensing venous blood temperature in the right ventricle of the heart is proposed in the Cook et al U.S. Pat. No. 4,43&,092.

As pointed out in the Alcidi U.S. Pat. No. 4,009,721, when an individual is engaging in muscular work or exerting a muscular effort, such as during exercise, the pH, the $pO_2$ and the $pCO_2$ of the human undergo a modification. More specifically, the pH and the $pO_2$ decrease and the $pCO_2$ increases. In view of this fact, Alcidi proposed monitoring the pH of the blood in the right atrium and to regulate the rate of stimulating pulses from a pacemaker in relation to the instantaneous variation of the pH of the blood.

Recently there has been proposed in the Bornzin U.S. Pat. No. 4,467,807 a rate adaptive demand pacemaker which alters the escape interval for demand pacing relative to a level of molecular oxygen in the oxygen-poor blood in the intracardiac or pulmonary artery. The molecular oxygen is sensed with an oxygen sensor, preferably of the type as disclosed in the Wirtzfeld et al U.S. Pat. Nos. 4,202,339 and 4,299,820. The Wirtzfeld et al patents teach measuring of oxygen saturation of blood using optical techniques. The transmissiveness of light through blood is used by Wirtzfeld et al to measure oxygen concentration. Bornzin teaches using such measurements for controlling the pacing of a heart.

It has also been proposed to provide a catheter which is capable of being inserted into a blood vessel and which has a gas permeable membrane and a pH sensor behind the membrane for measuring gases in the blood. Examples of such previously proposed catheters are disclosed in the following patents:

| U.S. Pat. No. | PATENTEE |
|---|---|
| 3,572,315 | Cullen II |
| 3,658,053 | Fergusson et al |
| 3,710,778 | Cornelius |

A percutaneous sensor for sensing $pO_2$ permeating from the skin is disclosed in the Parker U.S. Pat. No. 4,197,853.

A field-effect transistor for detecting the concentration of oxygen in a substance is disclosed in the Janata U.S. Pat. No. 4,198,851.

The need for measuring the concentration of oxygen in biological fluids has led to the development of several oxygen sensing devices such as the Clark oxygen electrode. Such electrodes are used in polarographic measurements of oxygen and typically include a silver electrode (cathode) and a reference electrode (anode) made of a silver/silver chloride composition which are immersed in an alkaline solution containing diffused $O_2$. An increasing voltage is applied to the cathode while the voltage of the reference electrode is maintained constant. A voltage-current curve generated in this manner will indicate the amount of diffusion of $O_2$ which is directly related to $pO_2$.

A catheter-mounted, oxygen polarographic electrode for use in testing of blood oxygen levels is disclosed in the Imredy U.S. Pat. No. 3,528,403.

Another cathode for polarographic measurements in a physiological medium such as human blood is disclosed in the Reichenberger U.S. Pat. No. 4,148,305.

Further, an electrode for measuring the concentration of oxygen gas, i.e. partial pressure of oxygen, in human blood is disclosed in the Uehara et al U.S. Pat. No. 4,442,841.

According to the teachings of the present invention, the partial pressure of oxygen $pO_2$, in the blood is measured and such measurement is used to control the rate of pacing of an implanted artificial pacemaker system. Such a pacer or pacemaker system differs from the teachings of the Bornzin U.S. Pat. No. 4,467,807 by the measuring of partial pressure of oxygen as opposed to sensing oxygen saturation, by the mounting of a $pO_2$ sensor in a pacing lead so that the partial pressure of oxygen in the blood in the heart is sensed and utilized for controlling the pacing of the heart.

Further differences in structure and operation of the apparatus and method of the present invention from the teachings of the various patents identified above will become apparent from the following description of the invention and the preferred embodiment thereof.

SUMMARY OF THE INVENTION

According to the invention there is provided an implantable apparatus for pacing a heart in accordance with the heart/pacer rate needed to produce a required cardiac output relative to the partial pressure of oxygen in the blood in the heart, $pO_2$, while the person having the apparatus implanted within his body is exercising, comprising:

a demand pacer, for implantation in the human body in a conventional manner, said pacer having control circuitry, a pulse gnerator coupled to said control circuitry and conventional sensing circuitry coupled to said control circuitry for sensing through a pacing lead heart electrical activity;

a pacing lead for implantation in a heart, said lead being mechanically and electrically coupled to a said placer and including a lead body having a conductor therein and a tip electrode thereon coupled to said conductor, said tip electrode being placeable in a ventricle of the heart for supplying pacing pulses to the heart, and said lead further having an opening therein which is located in a portion of the lead body that is proximal to said tip electrode and receivable in a heart;

$pO_2$ sensing means mounted in said opening for sensing the partial pressure (tension) of oxygen dissolved in the blood in a heart and for generating signals related to the $pO_2$ sensed;

conductor means in said lead coupled between said $pO_2$ sensing means and said control circuitry;

said control circuitry comprising a microprocessor including memory means for storing the relationship between $\Delta pO_2$ and $\Delta R$, a maximum rate increase allowed, $\Delta R_{Max.1}$, a minimum rate decrease allowed $\Delta R_{Max.2}$, a minimum programmed pacing rate $R_{Min.}$ and a maximum programmed pacing rate $R_{Max.L}$, means for

*relating a signal from the $pO_2$ sensing* means to the partial pressure of oxygen, $pO_2$, in the blood, means for determining changes in the partial pressure of oxygen, $\Delta pO_2$, and for relating such changes to a corresponding change in pacer rate, $\Delta R$, between the maximum rate increase allowed, $\Delta R_{Max.1}$, and the maximum rate decrease allowed, $\Delta R_{Max.2}$, means for adjusting the pacing rate R by adding $\Delta R$ to the present pacing rate R, to obtain a new pacing rate, R between the minimum programmed pacing rate $R_{Min.}$ and the maximum programmed pacing rate $R_{Max.}$, needed to supply a required cardiac output relative to the $pO_2$ measured, and means for causing the pacer to pace the heart at the newly calculated required pacing rate, R, when heart electrical activity is not sensed while the person is exercising.

Further according to the invention there is provided a method for pacing a heart in accordance with the heart/rate needed to produce a required cardiac output relative to the partial pressure of oxygen in the blood, $pO_2$, while a person, whose heart is being paced, is exercising, said method comprising the steps of:

implanting in a human body a demand pacer having control circuitry therein, a pulse generator coupled to said control circuitry and conventional sensing circuitry coupled to said control circuitry for sensing through a pacing lead heart electrical activity;

implanting in a heart a pacing lead having a conductor therein and a tip electrode coupled to the conductor;

placing the tip electrode in a ventricle of the heart;

electrically coupling the lead to the pacer;

providing an opening in a portion of the lead body which is proximal to the tip electrode and received in the heart;

mounting a $pO_2$ sensor in the opening for sensing the partial pressure (tension) of oxygen dissolved in the blood in the heart;

sensing the $pO_2$ in the heart with the $pO_2$ sensor;

determining with said control circuitry the partial pressure of oxygen $pO_2$, in the blood from signals from the $pO_2$ sensor;

storing the relationship between $\Delta pO_2$ and $\Delta R$, a maximum rate increase allowed, $\Delta R_{Max.1}$, a minimum rate decrease allowed $\Delta R_{Max.2}$, a minimum programmed pacing rate $R_{Min.}$ and a maximum programmed pacing rate $R_{Max.}$;

determining the required rate needed to supply a desired cardiac output relative to the sensed $pO_2$ including the steps of determining values of $pO_2$ sensed; determining changes in $pO_2$ sensed; relating the change, $\Delta pO_2$, to a corresponding change in heart rate, $\Delta R$, between the maximum rate increase allowed, $\Delta R_{Max.1}$, and the maximum rate decrease allowed, $\Delta R_{Max.2}$; adjusting the rate R by adding $\Delta R$ to the present pacing rate R to obtain a new pacing rate R between the minimum programmed pacing rate $R_{Min.}$ and the maximum programmed pacing rate $R_{Max.}$; and causing the pacer to pace the heart at the newly calculated required pacing rate R when heart electrical activity is not sensed while the person is exercising.

DESCRIPTION OF THE PREFERRED EMBODIMENT

Figure 1:
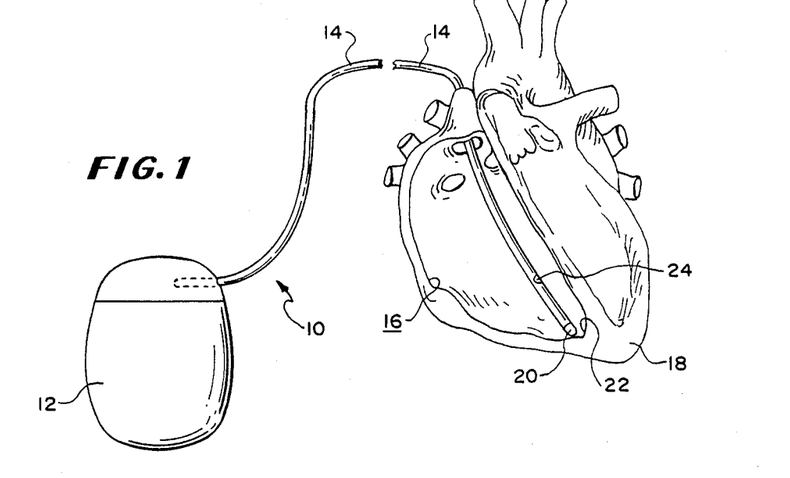
FIG. 1 is a diagram of the apparatus of the present invention for controlling the pacing rate of an implanted artificial pacer in response to the cardiac partial pressure of oxygen, $pO_2$, measured in the blood in the right ventricle of a heart in accordance with the teachings of the present invention and shows a heart, a pacing lead with a tip electrode thereof located at the apex of a right ventricle of the heart, a polarographic type $pO_2$ sensor mounted on the pacing lead and positioned near the tip electrode and in the right ventricle, and a pacer containing control circuitry for controlling the pacing rate in response to the $pO_2$ sensed.

Referring now to the drawings in greater detail, there is illustrated in FIG. 1 an apparatus 10 or pacer system 10 which is constructed according to the teachings of the present invention and which includes an implanted pacer or artificial pacemaker 12. The pacer 12 includes a pulse generator including amplifiers for sensing electrical cardiac activity, and control circuitry typically including a microprocessor, for processing signals and controlling pacing rate.

The pacer 12 is connected to a pacing lead 14 at the proximal end of the lead which extends pervenously into the right ventricle 16 of a heart 18 where a tip electrode 20 at the distal end of the lead 14 engages and stimulates the apex 22 of the right ventricle 16.

In accordance with the teachings of the present invention, a sensor 24 for sensing the partial pressure of oxygen, $pO_2$, in the blood in the heart, i.e., a $pO_2$ sensor 24, is mounted on the lead 14 so as to be located in the right ventricle just behind the tip electrode 20. This $pO_2$ sensor is connected to excitation and detection circuitry in the pacer 12 as will be described in greater detail below.

When a patient with sinus node disease has a pacing system implanted within his or her body with a pacing lead 14 implanted in his or her heart, such as in the right ventricle, such pacing system 10 stimulates the ventricle at a preset rate. In some patients the heart has lost its ability to increase ventricular rate with exercise. However, as the body engages in muscular activity, especially intense and prolonged muscular activity $pO_2$ in the blood decreases.

In accordance with the teachings of the present invention, the $pO_2$ in the blood in the ventricle 16 is sensed by the $pO_2$ sensor and the amount of $pO_2$ sensed is used for controlling the rate of application of pacing pulses to the tip electrode 20. This rate is referred to herein as the pacer rate, R. Thus, the system 10 uses $pO_2$ as a measure of exercise level.

Figure 3:
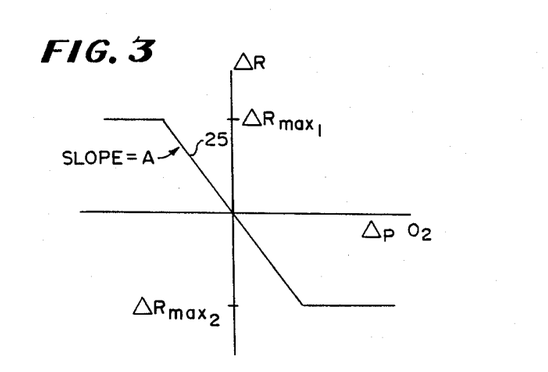
FIG. 3 is a graph showing the change in pacing rate, $\Delta R$, relative to $\Delta pO_2$.
Figure 3A:
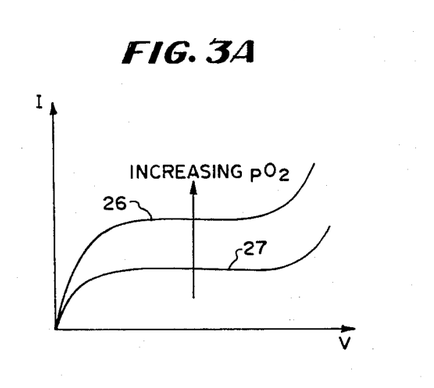
FIG. 3A is a graph of current versus voltage applied to a polarographic ($O_2$) sensor and shows the change in the current-voltage relationship for increasing values of $pO_2$.
Figures 8, 9:
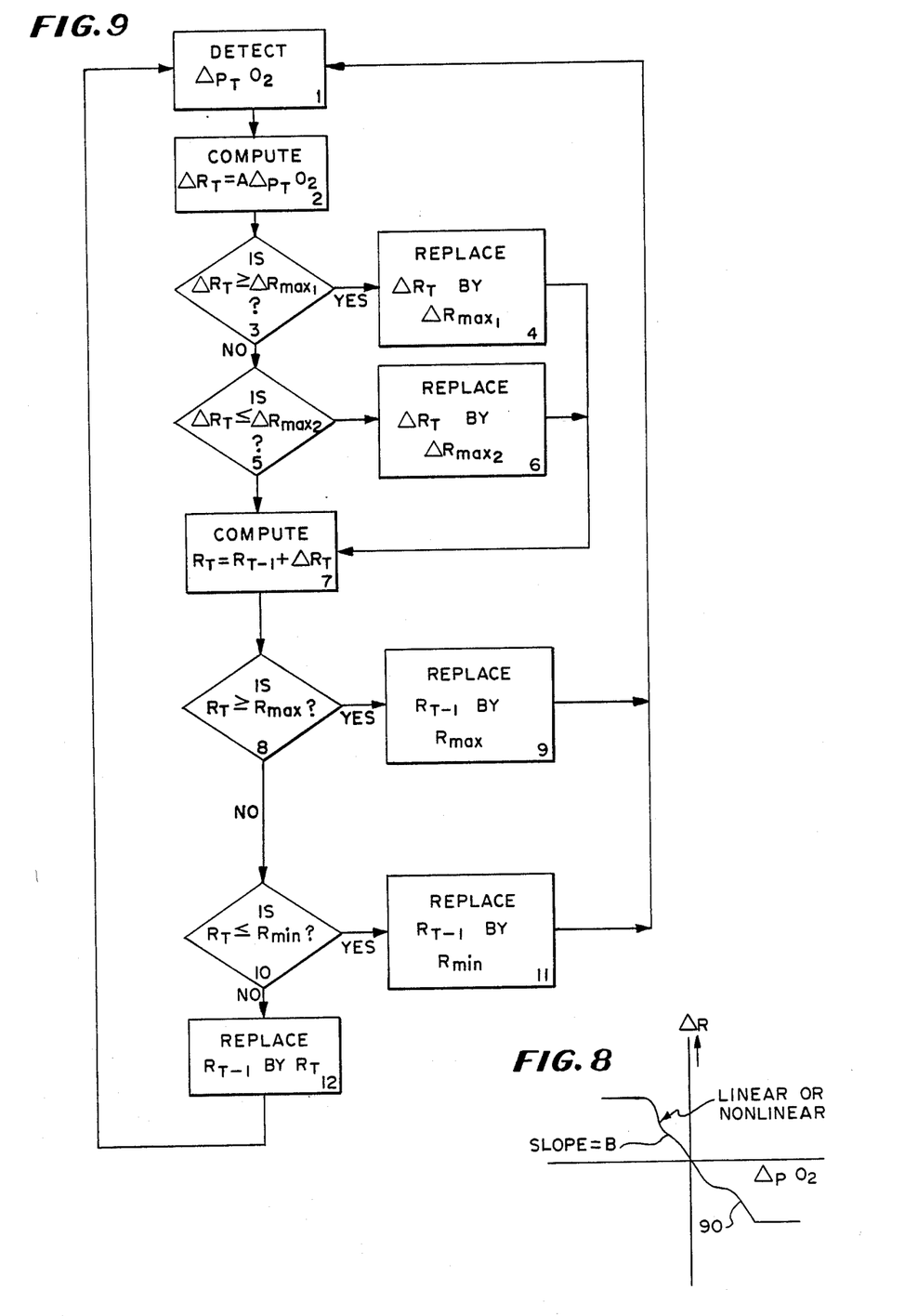
FIG. 8 is a graph of R versus $pO_2$ where the relationship between R and $pO_2$ is linear or nonlinear.
FIG. 9 is a flow chart of the program or routine carried out by the control circuitry (microprocessor) in the apparatus shown in FIG. 1 assuming a linear relationship between R and $pO_2$ as shown in FIG. 3.

As shown in FIG. 3, the relationship of the change in $pO_2$, $\Delta pO_2$, to the change in heart rate, $\Delta R$, can be assumed to be linear and shown by a line 25 with a slope equal to "A". Alternatively, the relationship of $\Delta pO_2$ to $\Delta R$ can be linear or nonlinear as shown in FIG. 8. The current-voltage curves 26 and 27 for two different values of $pO_2$ are shown in FIG. 3A where it will be appreciated that a lower steady state current in the flat portion of the curve 27 is obtained for a lower $pO_2$.

In either event, based upon the relationship between $\Delta pO_2$ and $\Delta R$, the pacer 12 can be adapted to exercise. More specifically, the rate of pulse generation or pacer rate can be controlled so that the pacing system 10 can be adapted for exercise based on measurements of $pO_2$ when an individual engages in exercise.

Figure 2:
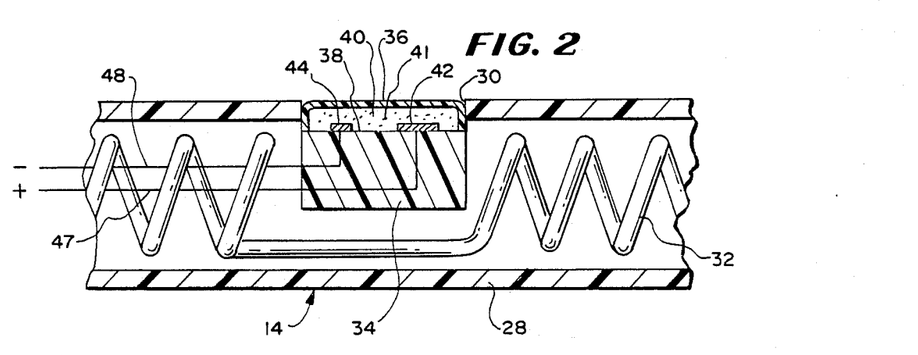
FIG. 2 is a longitudinal sectional view through the pacing lead shown in FIG. 1 and the $pO_2$ sensor mounted in the pacing lead and shows the sensor mounted in an opening in the lead.

In FIG. 2 there is shown an enlarged longitudinal cross section of the portion of the pacing lead 14 in which the $pO_2$ sensor 24 is mounted. Here it will be seen that the pacing lead 14 includes a tubular sheath 28 with an opening 30 in the sheath 28 in which the $pO_2$ sensor 24 is mounted.

Also mounted within the sheath 28 is a conventional coiled wire conductor or filar 32 for conducting senses cardiac electrical activity or stimulating pulses between the tip electrode 20 and the pacer 12.

The $pO_2$ sensor 24 shown in FIG. 2 is a polarographic ($O_2$) type sensor which includes a base or body 34 having a cap or cup-shaped gas-permeable membrane 36 mounted to a top surface 38 thereof so as to form a chamber 40 between the top surface 38 and the membrane 36. Typically, an alkaline solution 41 is placed in the chamber 40. The membrane 36 is oxygen permeable and can be made of silicone rubber.

A solid state reference electrode 42, typically made of silver/silver chloride, such as the reference electrode disclosed in the Zick et al U.S. Pat. No. 4,450,842 is mounted on the top surface 38. This electrode 42 forms an anode about which hydrogen ions collect.

A polarizing electrode 44 is also mounted on the top surface 38, spaced from the reference electrode 42. Typically, the electrode 44 is made of a noble metal, such as gold, platinum or silver and forms a cathode about which oxygen ions collect.

A conductor 47 is connected to the reference electrode 42 and extends through the tubular sheath 28 to the pacer 12. Likewise, a conductor 48 is connected to the polarizing electrode 44 and extends through the tubular sheath 28 to the pacer 12.

As a person exercises, the $pO_2$ in the blood in the right ventricle decreases resulting in less $O_2$ at the polarizing electrode 44 and a lower flat current over a certain voltage range as shown by curve 27 in FIG. 3A. The relationship of $\Delta pO_2$ to $\Delta R$ is assumed linear as shown in FIG. 3 and the change in heart/pacer rate over time as the patient or the person engages in exercise is shown by the curve 50 in FIG. 4.

Figure 4:
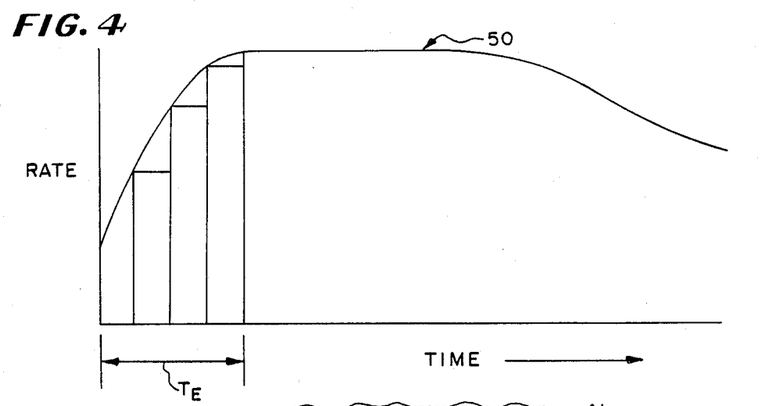
FIG. 4 is a graph of heart/pacer rate versus time while an individual is engaging in exercise.
Figure 5:
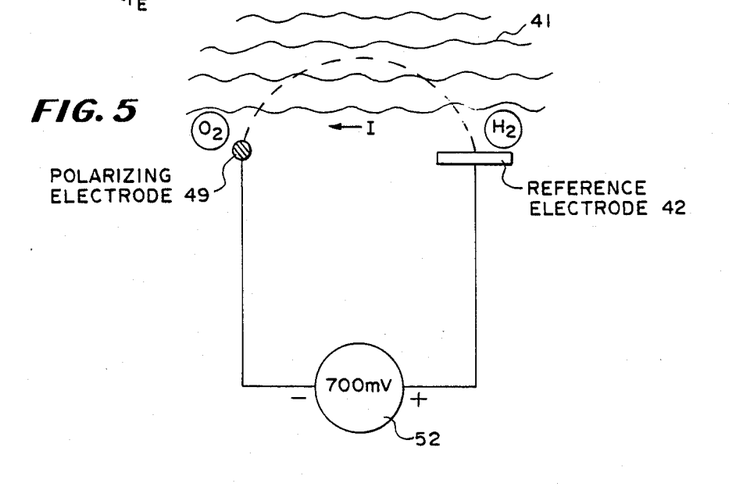
FIG. 5 is a schematic diagram of the electrodes and voltage applied across the electrode in the polarographic $pO_2$ sensor.

In the beginning of exercise during time, $T_E$, it is desirable to adjust the pacing rate frequently as shown in FIG. 4. According to the teachings of the present invention, this is achieved by applying pulses of approximately 700 mV from a voltage source 52 (located in the pacer 12) as shown in FIG. 5. The frequency and magnitude of the voltage pulses can be adjusted so as to establish clear measurable differences in polarizing current I relative to changes in $pO_2$.

Figure 6:
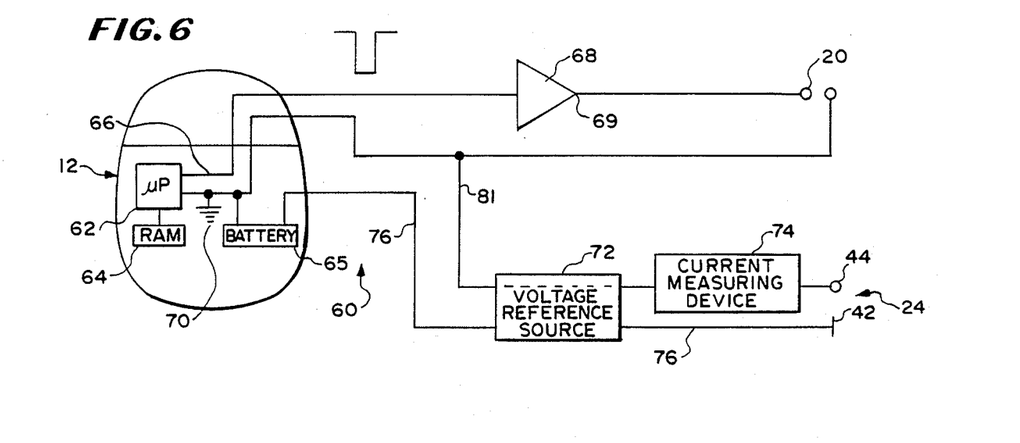
FIG. 6 is a schematic circuit diagram of the pacer system shown in FIG. 1.

One preferred control circuit 60 for use in the pacer system 10 is shown schematically in FIG. 6. Although some of the circuit elements are shown outside of the pacer 12 in FIG. 6, it is to be understood that such circuit elements most likely will be mounted in the pacer 12.

As shown, the control circuit 60 includes a microprocessor 62, a RAM 64 and a battery 65 mounted in the pacer 12. An output 66 from the microprocessor 62 is supplied to an amplifier 68 having an output 69 connected to the pacing tip electrode 20.

The ground 70 of the pacing circuit 60 is connected to a voltage reference source 72 and a current measuring device 74. The battery voltage is connected to this voltage reference source 72 and the current measuring device 74 via connector 76.

The voltage reference source 72 is connected to the polarizing electrode (cathode) 44 and the reference electrode (anode) 42 so that at least 500 mV can be established across the sensor cathode 44 and the anode 42. The current measuring device is connected to the polarizing electrode 44 and the output 76 of the voltage reference source. The measured current I, is used as an input signal for the system described in FIG. 7.

To reduce power consumed by this circuit 60, and therefore increase the longevity of the pacemaker 12, the circuit 60 is described in FIG. 6 can also be powered in an AC mode rather than in a DC mode.

Figure 6A:
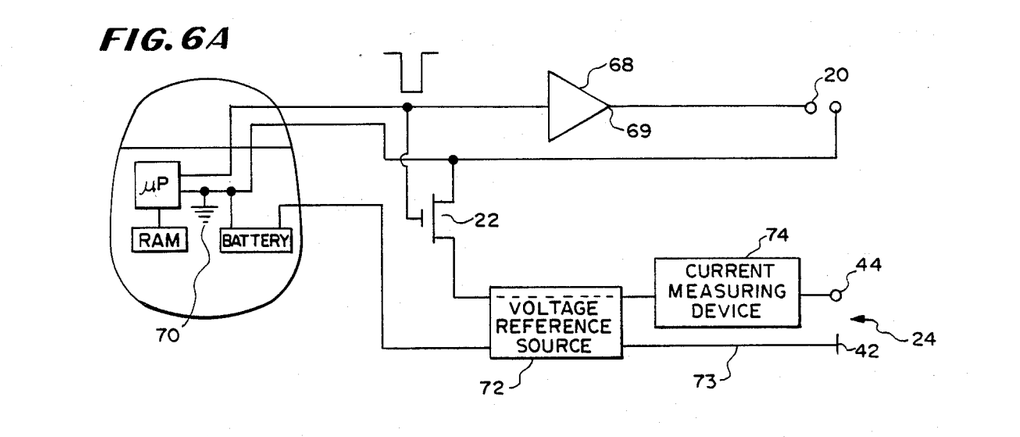
FIG. 6A is a schematic circuit diagram of a modified circuit for the pacer system shown in FIG. 1.

For operation in an AC mode, and as shown in FIG. 6A, the battery voltage is not supplied via conductor 81 but instead via a FET-switch 82 which is periodically opened and closed. The command signal for opening and closing the FET-switch 82 can even be the pacemaker pulse itself.

Figure 6B:
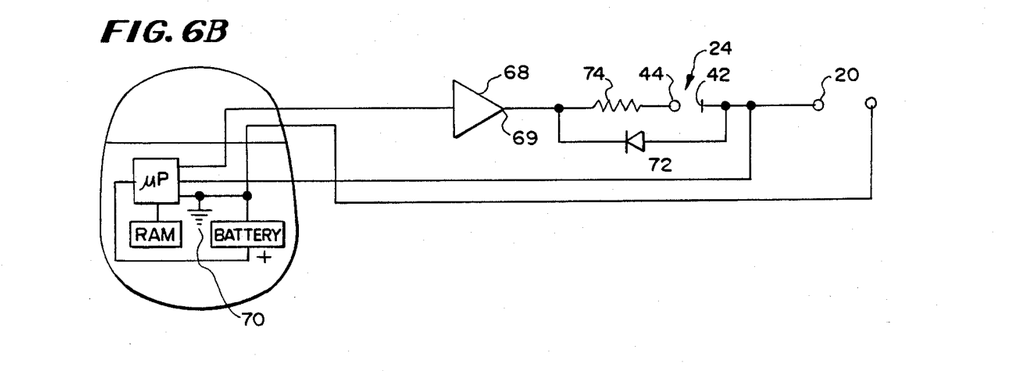
FIG. 6B is a schematic circuit diagram of another modified circuit for the pacer system shown in FIG. 1.

As shown in FIG. 6B, in its simplest form, the voltage reference source 72 is a diode 72 and the current measuring device 74 includes a resistor 74.

The sensor 24 is put in series with the output 69 of the amplifier 68. The resistor 74 is connected between the output 69 and the polarizing electrode 44. The reference electrode 42 is connected to the pacing tip electrode 20. The diode 72 is connected between output 69 and reference electrode 42.

The voltage across the resistor 74 is now proportional to the current flowing in a forward biased diode 72 giving a voltage of over 500 mV.

It may even be possible to use the pacing pulse for the sensor 24 which will minimize current or power drain on the pacer 12 while permitting effective pacing and adapting of pacer rate to exercise relative to change in blood $pO_2$.

Also, the pacer 12 can be a dual chambered pacer, such as a DDD pacer, where both chambers, the atrium and the ventricle, are paced and spontaneous electrical activity is sensed in both the chambers. Such a pacer has either a triggered or inhibited response, depending on the mode programmed by the physician.

Figure 7:
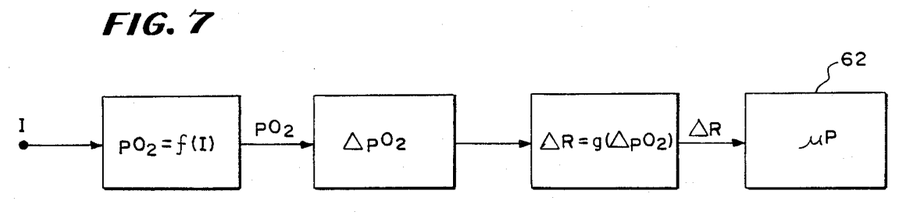
FIG. 7 is a block flow chart of the processing functions performed by the control circuitry of the pacer system in determining a desired change in pacing rate, R, from a measurement of the polarographic current, I.

Referring now to FIG. 7, the polarizing current I is first sensed and $pO_2$ as a function of I is calculated by the microprocessor 62. The $\Delta pO_2$ is calculated from $pO_2$. Next, $\Delta R$ as a linear function of $\Delta pO_2$ is calculated or $\Delta R$ as a non-linear function of $\Delta pO_2$ is retrieved from a look-up table stored in the RAM 64. Lastly, the newly calculated $\Delta R$ is supplied to the microprocessor 62 for causing it to change the pacer rate.

The relationship between $\Delta pO_2$ and $\Delta R$, for a normal heart, can be programmed in the form of an algorithm in the memory, RAM 64, of the microprocessor 62 or any other control circuitry mounted within the pacer 12. Typically, one will have a patient run on a treadmill to determine $pO_2$ and $\Delta pO_2$, relative to heart rate R and $\Delta R$, by comparing heart rate with measurements of $pO_2$ in the solution 41 for different levels of exercise.

Also, if the $pO_2$ sensor 24 should lose some of its sensitivity over time, the pacer system 10 can be reprogrammed via an in vivo calibration of the $pO_2$ sensor/pacer system utilizing the treadmill exercise procedure. However, a less direct but also precise calibration can be performed by only tuning the rate of the implanted pacer to the exercise level instead of calibrating the $pO_2$ sensing part of the system and the pacer part as described above. This method gives an overall calibration of the system.

Also, the current drain of the sensor 24 is reduced by the operation of the sensor 24 in a pulsating AC mode of operation rather than in a DC mode of operation. A.C. operation of electronic devices is known from the Ho U.S. Pat. No. 4,488,556, the disclosure of which is incorporated herein by reference. Empirical tests have shown that this may also improve the stability of the $pO_2$ sensor 24.

To avoid small oscillations a general filtering principle or an N-point averaging technique is employed. In this respect, N number of samples between 1 and 10, for example, are made and the average is chosen as the sampled peak $pO_2$. Then, this average is compared with the previously stored average of the peak $pO_2$ value to determine whether there has been a change. To simplify this explanation $pO_2$ is defined here as simply p. The change then is detected by measuring $\Delta p = p_x - (p_{x-1})$ where x equals the time order for a number of samples, N. Of course, to make this detection more reliable, one would detect, sense and determine $p_x - (p_{x-1})$, $(p_{x-1}) - (p_{x-2})$ and $(cp_{x-2}) - (p_{x-3})$. As a simplification, when all the differences have the same sign, the change is consistent. Then $\Delta p = p_x - (p_{x-1})$ and that is used as an input for the algorithm stored in the microprocessor within the pacer 12.

The algorithm or routine in its simplest form relates $\Delta R$ to $\Delta pO_2$. This can be realized in analog techniques but can also be realized in a digital manner assuming a linear relationship (FIGS. 3 and 8), or using a so-called "look-up" table based on the function of the curve 90 shown in FIG. 8.

The signal $\Delta pO_2$ serves as an input to the microprocessor 62 in the pacer 12 which serves to change the pacer rate frequency as a function of $\Delta pO_2$. Typically, an algorithm relationship of $\Delta pO_2$ to $\Delta R$, such as shown in FIG. 3 or FIG. 8, is stored in the memory, RAM 64, coupled to the microprocessor 62 in the pacer 12 and provides the algorithm, i.e., slope "A" of line 25 (FIG. 3), and the equation therefore, or slope "B" of the curve 90 (FIG. 8) and a look-up table, which is utilized by the control circuit 60.

In the event the sensor 24 or the circuit 60 within the pacer 12 malfunctions, the control circuit 60 can be caused to exit the program or routine and convert the pacer 12 to its standard non-exercise responsive function. Furthermore, if the peak pressure shows oscillation, the number N in the N-point averaging can be programmed or changed to a higher value and the circuitry for sensing or detecting a change in $pO_2$ can be programmed to take more samplings of differences before it decides that a change, $\Delta pO_2$, has occurred to cause a change in $\Delta R$.

In utilizing the apparatus 10 as shown in FIG. 1, certain parameters have to be determined experimentally and programmed into the microprocessor within the pacer 12. First of all, the linear relationship between heart rate and $\Delta pO_2$ between a programmed $\Delta R_{Max.1}$ and a programmed $\Delta R_{Max.2}$ of heart rate changes is estabklished and can be shown as the line having the slope "A" in FIG. 3. $\Delta R_{Max.1}$ is a maximum rate increase allowed wherein $\Delta R_{Max.2}$ is a maximum rate decrease allowed.

The linear graph of $\Delta R$ versus $\Delta pO_2$ has the equation $\Delta R = A \Delta pO_2$ between the limits $\Delta R_{Max.1}$ and $\Delta R_{Max.2}$. The slope "A", $\Delta R_{Max.1}$ and $\Delta R_{Max.2}$, $R_{Max.}$ (the maximum allowable pacer rate) and $R_{Min.}$ (the minimum allowable pacer rate) are all stored within the pacer's memory 64. Then, the above formula or algorithm is utilized in the program or routine carried out by the microprocessor 62 in the pacer 12. This routine for a linear or straight line relationship (line 25) between $\Delta R$ and $\Delta pO_2$ is set forth in the flow chart shown in FIG. 9.

The steps carried out by this program or routine are shown in FIG. 9 and are as follows:

STEP 1. Here the partial pressure change is detected, determined at a sampling time, T, and identified as $\Delta p_T O_2$.

STEP 2. Here $\Delta R$ is computedusing the equation: $\Delta R_T = -A(\Delta p_T O_2)$.

STEP 3. At this step, a determination is made whether $\Delta R_T$ is greater than or equal to $\Delta R_{Max.1}$.

STEP 4. If $R_T$ is greater than or equal to $R_{Max.1}$, the change in pacer rate $\Delta R_T$ is replaced by $\Delta R_{Max.1}$ and the program proceeds to STEP 7 for rate computation.

STEP 5. If the pacer rate change is not greater than or equal to $\Delta R_{Max.1}$, at STEP 5 a determination is made if $\Delta R_T$ is less than or equal to $\Delta R_{Max.2}$.

STEP 6. If the pacer rate chang $\Delta R_T$ is equal to or less than $\Delta R_{Max.2}$, the change in pacer rate $\Delta R_T$ is replaced by $\Delta R_{Max.2}$ and the program goes to STEP 7 for rate computation.

STEP 7. Here the proposed new pacing rate is computed from $R_T$ and $R_{T-1}$, which is the previously stored value.

STEP 8. Here a determination is made whether or not $R_T$ is greater than or equal to $R_{Max.}$.

STEP 9. If $R_T$ is equal to or greater than $R_{Max.}$, $R_{T-1}$ is replaced by $R_{Max.}$, which is used as a new rate value and the program loops back to STEP 1 for a new sampling.

STEP 10. If $R_T$ is less than $R_{Max.}$, a determination is made at STEP 10 whether or not $R_T$ is less than or equal to $R_{Min.}$.

STEP 11. If $R_T$ is less than or equal to $R_{Min.}$, then $R_{T-1}$ is replaced by $R_{Min.}$ and the program loops back to STEP 1 for a new sampling.

STEP 12. If $R_T$ is not less than or equal to $R_{Min.}$, the pacing rate is set to the calculated value of $R_T$ or the closest programmable value and the program returns to STEP 1.

As shown in FIG. 8, the relationship between $\Delta R$ and $\Delta pO_2$ may not be linear. In such a situation, it is preferable to use a look-up table rather than to determine some formula for the nonlinear slope "B" of the graph shown in FIG. 8.

Figure 10:
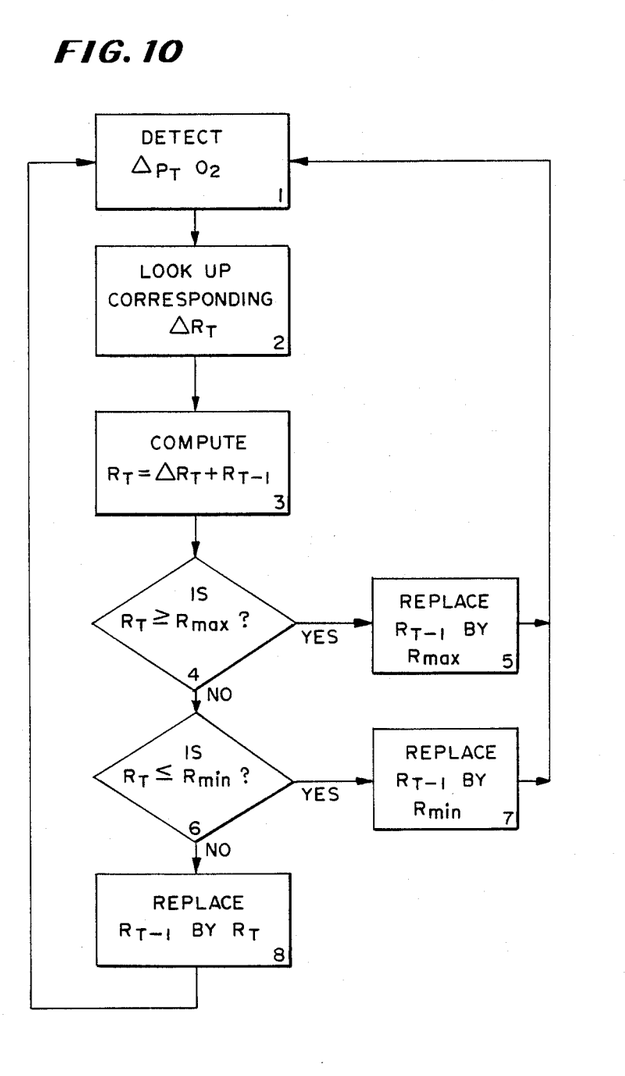
FIG. 10 is a flow chart of a program or routine carried out by the control circuitry (microprocessor) of the apparatus shown in FIG. 1 which uses a look-up table for determining a R corresponding to a $pO_2$ for both linear and nonlinear relationships between changes of R and $pO_2$, as shown in FIG. 8.

Thus, with reference to the graph shown in FIG. 8 of the $\Delta R$ versus $\Delta pO_2$ it is possible for the corresponding values of points on the curve or graph 90 having the nonlinear slope "B" to be stored in a memory, e.g. RAM 64, along with $R_{Max.}$, and $R_{Min.}$. Then, the steps of the program or routine carried out by the microprocessor 62 in the pacer 12 are as shown in FIG. 10 and are as follows:

STEP 1. Here the partial pressure change $\Delta p_T O_2$ at a sampling time T is detected and determined.

STEP 2. From the look-up table, $\Delta R_T$ is found at STEP 2.

STEP 3. Here the proposed new pacing rate $R_T$ is calculated from the previously stored value $R_{T-1}$ and $\Delta R_T$.

STEP 4. At this step, a determination is made whether or not the rate $R_T$ is greater than or equal to $R_{Max.}$.

STEP 5. If $R_T$ is greater than or equal to $R_{Max.}$, $R_{T-1}$ is replaced by $R_{Max.}$ and the program loops back to STEP 1 for a new sampling.

STEP 6. If Rhd T is less than $R_{Max.}$, a determination is made if $R_T$ is less than or equal to $R_{Min.}$.

STEP 7. If $R_T$ is less than or equal to $R_{Min.}$, $R_{T-1}$ is replaced by $R_{Min.}$ and the program loops back to STEP 1.

STEP 8. If $R_T$ is greater than $R_{Min.}$, the pacer rate is set equal to the calculated value or the nearest programmable value and the program loops back to STEP 1 for the next sample.

Figure 11:
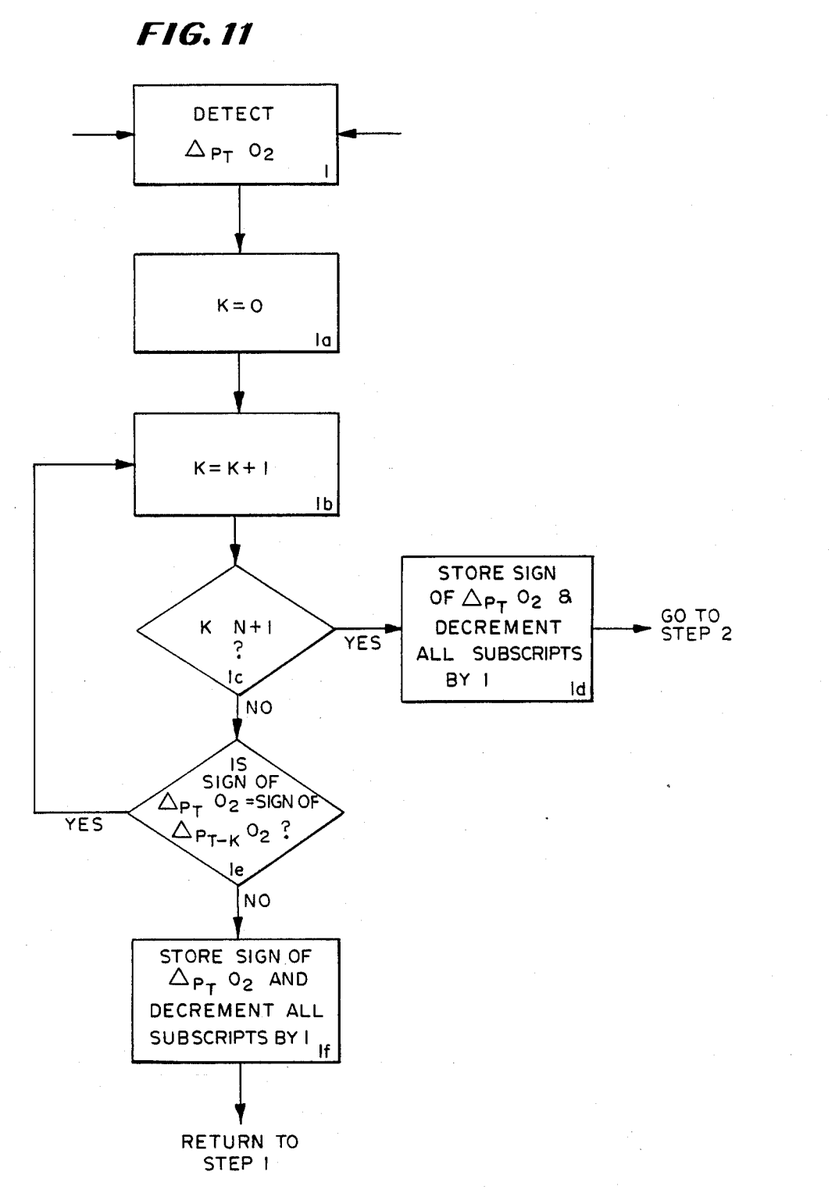
FIG. 11 is a flow chart of a subroutine that can be carried out by the control circuitry (microprocessor) of the apparatus shown in FIG. 1 to provide smoothing of the heart/pacer rate changes by smoothing the changes in $pO_2$, and is inserted between steps 1 and 2 of the routine or program shown in FIG. 8 or FIG. 10.

If desired, a smoothing subroutine may be incorporated into the programs or routines shown in FIGS. 9 and 10 and the flow chart for such a subroutine is shown in FIG. 11. This subroutine may be able to protect against various changes in sign of $\Delta p_T O_2$ by only accepting its value if its sign is the same as that of the N−1 previous samples.

The smoothing subroutine is inserted between STEPS 1 and 2 of either of the routines illustrated in FIGS. 9 and 10 as indicated in FIG. 11.

The steps of this subroutine are as follows:

STEPS 1a, 1b and 1c. Here a counting procedure is undertaken where at STEP 1a a count K=0 and at STEP 1b the count is $K=K+1$ followed by a determination at STEP 1c if $K=N+1$.

STEP 1d. If $K=N+1$, the sign of $\Delta p_T O_2$ is stored and all subscripts are decremented by 1.

STEP 1e. If K is not equal to N+1, a determination is made whether or not the sign of $\Delta p_T O_2$ equals the sign of $\Delta p_{T-K}(O_2)$. If the answer is yes, the program loops back to STEP 1b.

STEP 1f. If the answer is no, the sign of $\Delta p_T O_2$ is stored and all subscripts are decremented by 1. From STEP 1f, the program loops back to STEP 1.

From the foregoing description, it will be apparent that the apparatus 10 of the present invention and the method for using same provide a simple and practical means for adjusting the pacing rate of a pacing system relative to changes in partial pressure of oxygen $pO_2$, in the blood in the heart as a patient with the implanted pacer system 10 is undergoing exercise.

Also, it will be apparent that modifications can be made to the apparatus and method of the present invention without departing from the teachings of the invention. Accordingly, the scope of the invention is only to be limited as necessitated by the accompanying claims.

We claim:

1. An implantable apparatus for pacing a heart in accordance with the heart/pacer rate needed to produce a required cardiac output relative to the partial pressure of oxygen in the blood in the heart, $pO_2$, while the person having the apparatus implanted within his body is exercising, comprising:

a demand pacer, for implantation in the human body in a conventional manner, said pacer having control circuitry, a pulse generator coupled to said control circuitry and conventional sensing circuitry coupled to said control circuitry for sensing through a pacing lead heart electrical activity;

a pacing lead for implantation in a heart, said lead being mechanically and electrically coupled to said pacer and including a lead body having a conductor therein and a tip electrode thereon coupled to said conductor, said tip electrode being placeable in a ventricle of the heart for supplying pacing pulses to the heart, and said lead having an opening therein which is located in a portion of the lead body that is proximal to said tip electrode and receivable in a heart;

$pO_2$ sensing means mounted in said opening for sensing the partial pressure (tension) of oxygen dissolved in the blood in a heart and for generating signals related to the $pO_2$ sensed;

condutor means in said lead coupled between said $pO_2$ sensing means and said control circuitry;

said control circuitry comprising a microprocessor including memory means for storing the relationship between $\Delta pO_2$ and $\Delta R$, a maximum rate increase allowed, $\Delta R_{Max.1}$, a minimum rate decrease allowed $\Delta R_{Max.2}$, a minimum programmed pacing rate $R_{Min.}$ and a maximum programmed pacing rate $R_{Max.}$, means for relating a signal from the $pO_2$ sensing means to the partial pressure of oxygen, $pO_2$, in the blood, means for determining changes in the partial pressure of oxygen, $\Delta pO_2$, and for relating such changes to a corresponding change in pacer rate, $\Delta R$, between the maximum rate increase allowed, $\Delta R_{Max.1}$, and the maximum rate decrease allowed, $\Delta R_{Max.2}$, means for adjusting the pacing rate R by adding $\Delta R$ to the present pacing rate R, to obtain a new pacing rate, R, between the minimum programmed pacing rate $R_{Min.}$ and the maximum programmed pacing rate $R_{Max.}$, needed to supply a required cardiac output relative to the $pO_2$ measured, and means for causing the pacer to pace the heart at the newly calculated required pacing rate, R, when heart electrical activity is not sensed while the person is exercising.

2. The apparatus of claim 1 wherein said control circuitry includes means for smoothing out changes in $pO_2$, and means for determining when there has been a change in sign between samplings of $pO_2$ and calculations of $\Delta pO_2$ to detect an inconsistent change.

3. The apparatus of claim 1 wherein said $pO_2$ sensing means comprise a chamber having a liquid solution therein, an $O_2$-permeable membrane across an opening of said chamber, a polarizing electrode in said chamber and a reference electrode in said chamber.

4. The apparatus of claim 3 wherein said liquid solution is an alkaline solution.

5. The apparatus of claim 3 wherein said $O_2$-permeable membrane is made of silicone rubber.

6. The apparatus of claim 3 wherein said polarizing electrode is made of silver.

7. The apparatus of claim 3 wherein said reference electrode is made of a silver/silver chloride composition.

8. The apparatus of claim 3 wherein said control circuitry is coupled to both said $pO_2$ sensor and said tip electrode and includes means for periodically energizing said $pO_2$ sensor with pacing pulses that are supplied to said tip electrode.

9. The apparatus of claim 3 wherein said control circuitry includes a power source having a system ground and being coupled to said microprocessor, and a voltage reference source coupled to said power source and coupled to said microprocessor, and said apparatus includes a current measuring device coupled between said voltage reference source and said polarizing electrode, said voltage reference source also being coupled to said reference electrode.

10. The apparatus of claim 9 including an output amplifier, an input of said output amplifier being coupled to the pacing pulse output of said microprocessor and an output of said output amplifier being connected to said tip electrode.

11. The apparatus of claim 9 including an electrical switch connected between system ground and the voltage reference source for causing intermittent energization of said $pO_2$ sensing means.

12. The apparatus of claim 9 wherein said measuring device includes a resistor.

13. The apparatus of claim 9 wherein said voltage reference source maintains a control voltage and includes a diode connected across said reference electrode and said polarizing electrode.

14. The apparatus of claim 9 wherein said power source is a battery having a positive terminal and a negative terminal, one terminal of said battery being coupled to the system ground and the other terminal being coupled to said reference electrode, said system ground being coupled to said polarizing electrode through said current measuring device, said voltage reference source including a diode connected between said reference electrode and said polarizing electrode, and said current measuring device including a resistor coupled between said diode and said polarizing electrode.

15. The apparatus of claim 14 wherein said microprocessor has a pacing pulse output and said apparatus includes an electronic switch having a base and being coupled between said system ground and said diode, and said base being coupled to said pacing pulse output of said microprocessor whereby said $pO_2$ sensor is only energized when a pacing pulse is generated.

16. The apparatus of claim 9 wherein said microprocessor has a pacing pulse output and said current measuring device includes a resistor coupled between said output and said polarizing electrode, said reference electrode being connected to said tip electrode and said reference voltage source including a diode connected at one end to the connection between said reference electrode and said tip electrode and at the other end to the connection between said resistor and said output.

17. A method for pacing a heart in accordance with the heart/rate needed to produce a required cardiac output relative to the partial pressure of oxygen in the blood, $pO_2$, while a person, whose heart is being paced, is exercising, said method comprising the steps of:

implanting in a human body a demand pacer having control circuitry therein, a pulse gnerator coupled to said control circuitry and conventional sensing circuitry coupled to said control circuitry for sensing through a pacing lead heart electrical activity;

implanting in a heart a pacing lead having a conductor therein and a tip electrode coupled to the conductor;

placing the tip electrode in a ventricle of the heart;

electrically coupling the lead to the pacer;

providing an opening in a portion of the lead body which is proximal to the tip electrode and received in the heart;

mounting a $pO_2$ sensor in the opening for sensing the partial pressure (tension) of oxygen dissolved in the blood in the heart;

sensing the $pO_2$ in the heart with the $pO_2$ sensor;

determining with said control circuitry the partial pressure of oxygen $pO_2$, in the blood from signals from the $pO_2$ sensor;

storing the relationship between $\Delta pO_2$ and $\Delta R$, a maximum rate increase allowed, $\Delta R_{Max.1}$, a minimum rate decrease allowed $\Delta R_{Max.2}$, a minimum programmed pacing rate $R_{Min.}$ and a maximum programmed pacing rate $R_{Max.}$;

determining the required rate needed to supply a desired cardiac output relative to the sensed $pO_2$ including the steps of determining values of $pO_2$ sensed; determining changes in $pO_2$ sensed; relating the change, $\Delta pO_2$, to a corresponding change in heart rate, $\Delta R$, between the maximum rate increase allowed, $\Delta R_{Max.1.}$, and the maximum rate decrease allowed, $\Delta R_{Max.2}$; adjusting the rate R by adding $\Delta R$ to the present pacing rate R to obtain a new pacing rate R between the minimum programmed pacing rate $R_{Min.}$ and the maximum programmed pacing rate $R_{Max.}$; and causing the pacer to pace the heart at the newly calculated required pacing rate R when heart electrical activity is not sensed while the person is exercising.

18. The method claim 17 including the steps of:

employing a smoothing technique to average changes in partial pressure of oxygen, $\Delta pO_2$; and determining when there has been a change in sign between samplings of $\Delta pO_2$ indicating an inconsistent change;

19. The method of claim 11 including the step of providing in said $pO_2$ sensor a chamber having a liquid solution therein, an $O_2$-permeable membrane across an opening of said chamber, a polarizing electrode in said chamber and a reference electrode in said chamber.

20. The method of claim 11 including the step of periodically energizing said $pO_2$ sensor with pacing pulses that are also supplied to said tip electrode.

21. The method of claim 11 including the step of supplying voltage pulses across said polarizing electrode and said reference electrode.

22. The method of claim 11 wherein said step of relating the sensed $pO_2$ with the required heart rate comprises the steps of:

measuring the $pO_2$ at a first point in time;
computing the incremental change in $pO_2$;

$$\Delta pO_2 = pO_{2T} - (pO_{2T-1});$$

looking up the corresponding $\Delta R$ in the stored look-up table of heart rates relative to various values of $pO_2$;
computing the required heart rate $R_T = \Delta R + (R_{t-1})$;
determining whether the computed heart rate is equal to or above the maximum programmed pacer rate or is equal to or below the minimum programmed pacer rate; and
if the calculated heart rate meets either of these conditions, replacing the pacer rate $R_{T-1}$ by either the maximum programmed pacer rate or minimum programmed pacer rate stored in a memory and replacing the last sensed $pO_2$ with the newly sensed $pO_2$ value;
if the heart rate calculated is between the maximum and minimum programmed pacer rates stored in a memory, replacing the last pacing rate by the newly computed heart rate and replacing the last $pO_2$ value by the newly measured $pO_2$ value; and
adjusting the pacer rate to the value of the pacer rate just calculated.

23. The method of claim 22 including the step of smoothing heart rate changes by smoothing changes in $pO_2$.

24. The method of claim 23 wherein the step of smoothing comprises:

comparing the sign of the result, $\Delta pO_2$ with the sign of the $N-1$ previously computed differences which have been stored; if there is no sign change in N consecutive samples, determining the appropriate rate changes; if the sign of the present increments of $\Delta pO_2$ is equal to the sign of the previous $N-1$ increments in $pO_2$ incrementing another increment of $\Delta pO_2$ for the next comparison; and, if the sign changes indicating an inconsistent change, storing the new sign in the memory and returning to the initial step of measuring $pO_2$.

25. The method of claim 24 including the step of basing the rate change on the average value of $\Delta pO_2$ over the N most recent samples if no sign change has occurred.

* * * * *